United States Patent [19]

Merkle et al.

[11] Patent Number: 5,795,983
[45] Date of Patent: Aug. 18, 1998

[54] PREPARATION OF AMMONIUM SALTS OF 3-ISOPROPYL-2, 1, 3-BENZOTHIA-DIAZIN-4-ONE 2,2-DIOXIDE

[75] Inventors: Hans Rupert Merkle, Ludwigshafen; Alfons Durein, Römerberg; Hanspeter Hansen, Ludwigshafen; Karl-Friedrich Jäger, Limburgerhof, all of Germany

[73] Assignee: BASF Aktiengesellschaft, Ludwigshafen, Germany

[21] Appl. No.: 894,157

[22] PCT Filed: Feb. 1, 1996

[86] PCT No.: PCT/EP96/00420

§ 371 Date: Aug. 15, 1997

§ 102(e) Date: Aug. 15, 1997

[87] PCT Pub. No.: WO96/25407

PCT Pub. Date: Aug. 22, 1996

[30] Foreign Application Priority Data

Feb. 15, 1995 [DE] Germany .................. 195 05 036.3

[51] Int. Cl.$^6$ ........................... C07D 285/16
[52] U.S. Cl. ........................... 544/11
[58] Field of Search ........................... 544/11

[56] References Cited

U.S. PATENT DOCUMENTS 3,012,870  12/1961  Rechter ................. 71/2.6
5,266,553  11/1993  Champion et al. ....... 504/206

FOREIGN PATENT DOCUMENTS 1542836   4/1971   Germany.
2164459   7/1973   Germany.
2 217722  10/1973  Germany.
27 10 382 9/1978   Germany.

OTHER PUBLICATIONS

Kirk–Othmer: "Encyclopedia of Chemical Technology. 4$^{th}$ed., vol. 2" 1992. John Wiley & Sons, New York XP002007803.

*Primary Examiner*—John M. Ford
*Attorney, Agent, or Firm*—Oblon, Spivak, McClelland, Maier & Neustadt, P.C.

[57] ABSTRACT

A process for preparing salts of 3-isopropyl-2,1,3-benzothia-diazin-4-one 2,2-dioxide of the general formula I

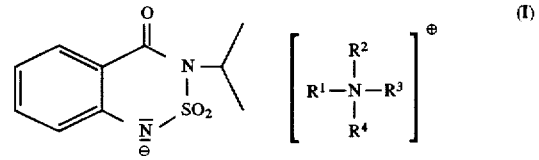

($R^1$–$R^4$=H, lower alkyl, lower hydroxyalkyl) by reacting bentazone (IIa) with an amine IIIa in an organic solvent, by reacting bentazone (IIa) with an amine IIIa or an ammonium salt IIIb in a virtually water-immiscible organic solvent and taking up the salt I in water or by reacting bentazone (IIa) with an ammonium salt IIIb or bentazone-sodium (IIb) with an ammonium salt IIIc, in each case in water.

9 Claims, No Drawings

PREPARATION OF AMMONIUM SALTS OF 3-ISOPROPYL-2, 1, 3-BENZOTHIA-DIAZIN-4-ONE 2,2-DIOXIDE

This is a 371 of PCT/EP96/00420, filed Feb. 1, 1996.

BACKGROUND OF THE INVENTION

1. Field of the Invention

The present invention relates to processes for preparing salts of 3-isopropyl-2,1,3-benzothiadiazin-4-one 2,2-dioxide of the general formula I

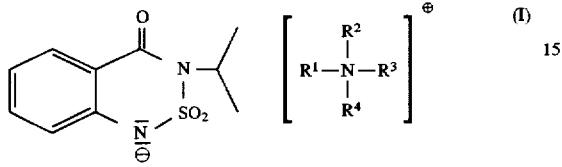

where the radicals $R^1$, $R^2$, $R^3$ and $R^4$ independently of one another are hydrogen, lower alkyl or lower hydroxyalkyl.

2. Description of the Background

Herbicidal benzothiadiazin-4-one 2,2-dioxides are disclosed in DE-A 15 42 836, DE-A 21 64 459 and DE-A 22 17 722. Ammonium salts are also mentioned therein as an application form, the ammonium, methylammonium, trimethylammonium, ethylammonium, diethanolammonium and ethanolammonium salts being particularly mentioned.

It is furthermore generally known that the sodium salt, the calcium salt and the potassium salt of 3-isopropyl-2,1,3-benzo-thiadiazin-4-one 2,2-dioxide (INN name: bentazone) are very hygroscopic. In the case of solid formulations of these salts, this leads to the product forming lumps as a result of atmospheric humidity or even deliquescing and thereby no longer being meterable without problems.

If these salts are introduceed into water-soluble film bags, the latter are furthermore dehydrated by interaction of the hygroscopic active compounds with the films. This results in the films becoming brittle, ie. their storage stability is no longer guaranteed.

In the synthesis of bentazone, the active compound is customarily obtained in neutral form and as a rule dissolved in an organic solvent (cf. DE-A 27 10 382).

Usually, the active compound is then converted into one of its salts, as these improve the bioavailability of bentazone.

U.S. Pat. No. 5 266 553 discloses, for example, the formulation of ammonium salts of bentazone as flowable water-soluble solids. For this purpose, according to the general description in the patent an aqueous mixture of the ammonium salt is first prepared. The solid formulation of the active compound is obtained from this by evaporating all of the solvent and subjecting the product to aftertreatment with a neutralizing base. The evaporation step with concomitant use of water as a solvent, however, necessitates a high expenditure of energy and the active compound is exposed during the course of this to the increased evaporation temperature for a very long time.

SUMMARY OF THE INVENTION

It is an object of the present invention to provide processes for preparing ammonium salts of bentazone in which the disadvantages of the preparation process described above are avoided completely or in part.

We have found that this object is achieved by a process for preparing salts of 3-isopropyl-2,1,3-benzothiadiazin-4-one 2,2-dioxide of the general formula I

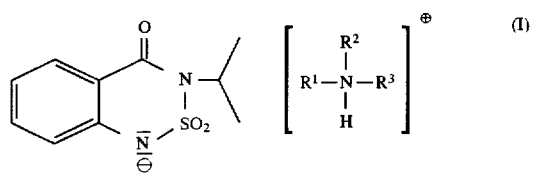

where the radicals $R^1$, $R^2$ and $R^3$ independently of one another are hydrogen, lower alkyl or lower hydroxyalkyl, which comprises reacting 3-isopropyl-2,1,3-benzothiadiazin-4-one 2,2-dioxide (IIa)

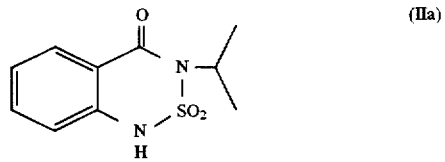

in an organic solvent with an amine of the general formula IIIa

We have additionally found a process for preparing salts of 3-isopropyl-2,1,3-benzothiadiazin-4-one 2,2-dioxide of the general formula I

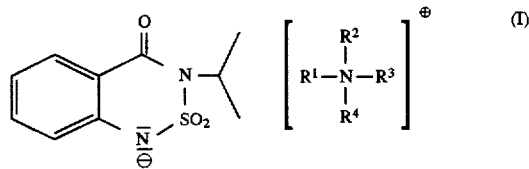

where the radicals $R^1$, $R^2$, $R^3$ and $R^4$ independently of one another are hydrogen, lower alkyl or lower hydroxyalkyl, which comprises a) reacting 3-isopropyl-2,1,3-benzothiadiazin-4-one 2,2-dioxide (IIa)

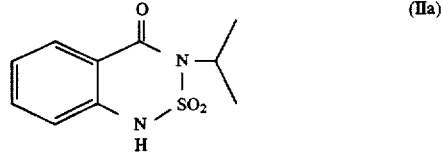

in a virtually water-immiscible organic solvent and, if desired, in the presence of water, with an amine of the general formula IIIa

or an ammonium salt of the general formula IIIb

where X is the anion of an acid of $pK_A$ greater than 4 or the hydroxyl ion and n is equal to the number of negative charges on the anion X, and b) taking up the salt I in water.

Moreover, we have found a process for preparing salts of 3-isopropyl-2,1,3-benzothiadiazin-4-one 2,2-dioxide of the general formula I

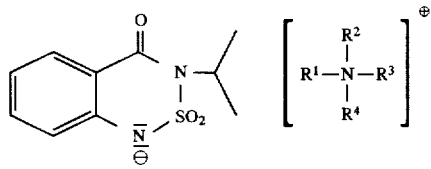

where the radicals $R^1$, $R^2$, $R^3$ and $R^4$ independently of one another are hydrogen, lower alkyl or lower hydroxyalkyl, which comprises a) reacting 3-isopropyl-2,1,3-benzothiadiazin-4-one 2,2-dioxide (IIa)

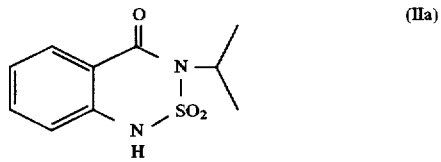

in water with an ammonium salt of the general formula IIIb

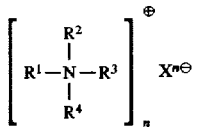

where X is the anion of an acid having a $pK_A$ greater than 4 or the hydroxyl ion and n is equal to the number of negative charges on the anion X, or b) reacting the sodium salt of bentazone (IIb)

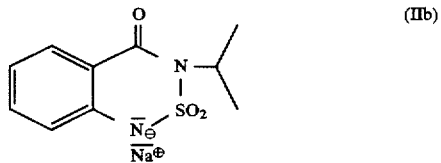

in water with an ammonium salt of the general formula IIIc

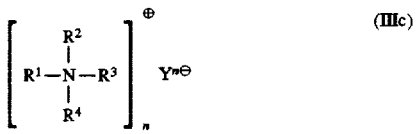

where Y is the anion of an acid and n is equal to the number of negative charges on the anion Y.

DETAILED DESCRIPTION OF THE INVENTION

Lower alkyl or lower hydroxyalkyl are understood as meaning alkyl groups or hydroxyalkyl groups having up to 8, preferably having up to 6, C atoms, such as methyl, hydroxymethyl, ethyl, 2-hydroxyethyl, propyl, 3-hydroxypropyl and butyl.

The processes according to the invention are called processes A, B and C in the following.

Process A

In process A, bentazone (IIa) is reacted in an organic solvent with an amine IIIa (see scheme 1).

The amines IIa are generally known.

As a rule, the amine IIIa is employed in an equimolar amount, based on bentazone (IIa). It can be advantageous for completing the reaction to use the amine IIIa in an excess. However, to achieve a complete conversion this excess in general does not need to exceed 10 mol %, based on IIa.

Suitable organic solvents are: aromatic hydrocarbons, preferably mono- to trimethylated benzenes, especially toluene and the xylenes; ketones, preferably having 3 to 9 C atoms, in particular acetone; esters, preferably of monocarboxylic acids having 1 to 5 C atoms with monoalkanols having 1 to 4 C atoms, especially ethyl acetate; ethers, preferably having 4 to 8 C atoms, especially tetrahydrofuran; haloalkanes, preferably mono- or dichloroalkanes having 2 to 4 C atoms, especially 1,2-dichloroethane, and in addition alkanols, preferably $C_1$—$C_4$-alkanols, especially methanol or ethanol, and also mixtures of two or more of the abovementioned solvents.

The solvent used particularly advantageously is 1,2-dichloroethane per se.

Scheme 1

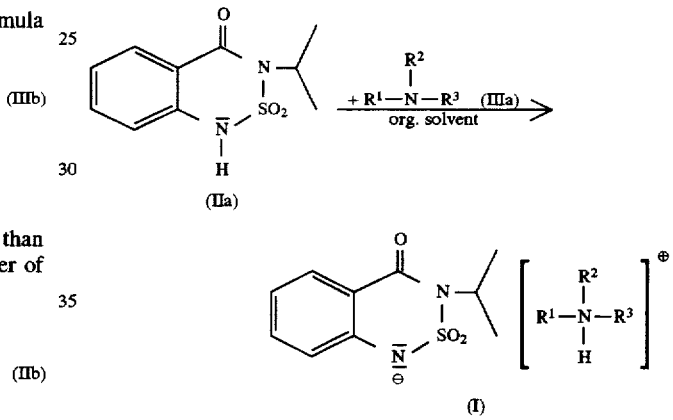

$R^1$-$R^3$ = independently of one another, H, lower alkyl or lower hydroxyalkyl Based on one mol of bentazone (IIa), normally from 0.2 to 25 and especially from 1 to 10 kg of solvent are used. The bentazone (IIa) can in this case contain up to 2% by weight of water without this being detrimental to the process.

The process can be carried out at from 10° to 80° C. The temperature during the reaction especially has an effect on the solubility of the bentazone (IIa), which increases with the temperature.

Especially in those cases in which gaseous or low-boiling amines IIIa are involved, the temperature, however, should not exceed a value of 60° C. The reaction is preferably carried out at from 20° to 60° C., and in particular from 25° to 50° C.

The reaction is in general carried out at from 0.5 to 10 bar, preferably from 1 to 3 bar, and in particular at normal pressure (atmospheric pressure).

Suitable reactors are the apparatuses customarily suitable for reactions of this type.

The salt I precipitates at the reaction temperature and/or on cooling the mixture and can be separated off from the liquid phase in manner which is known per se, especially by filtration. The yield of salt I is from 95 to 100%.

Process A is particularly suitable for preparing the $NH_4^+$ salt of bentazone (I; $R^1$-$R^4$=H).

A procedure is preferably used here in which ammonia gas is passed directly into the solution of bentazone (IIa) in the organic solvent or in which the solution of bentazone (IIa) in the organic solvent is treated with aqueous ammonia.

Process B

In this process, bentazone (IIa) is reacted with an amine IIIa or an ammonium salt IIIb in a virtually water-immiscible organic solvent, if desired in the presence of water, and the salt I is taken up in water (see scheme 2).

the amines IIIa or the ammonium salts IIIb is preferably carried out at from 20° to 60° C., and in particular from 25° to 50° C.

The reaction is in general carried out at a pressure from 0.5 to 10 bar, preferably from 1 to 3 bar, and in particular at normal pressure (atmospheric pressure).

Suitable reactors are the apparatuses customarily suitable for reactions of this type.

The salt I formed is taken up in water, it being possible to add this during the reaction or only at the end of the reaction.

Scheme 2

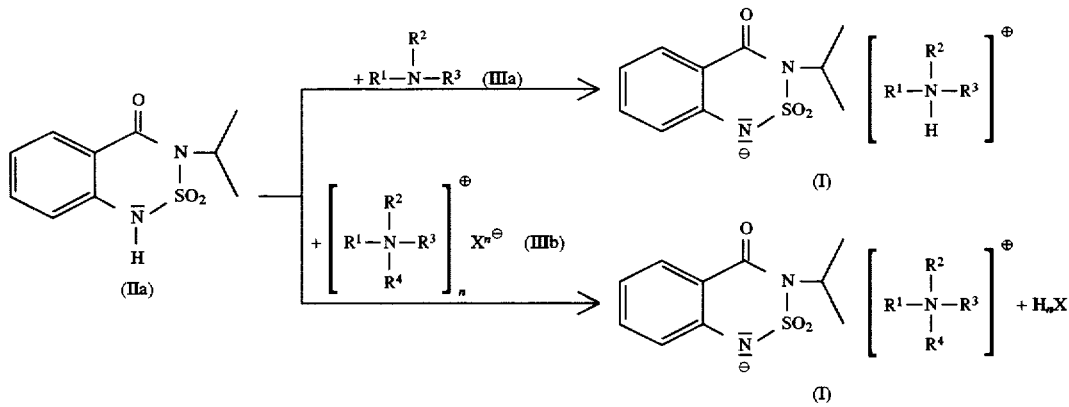

$R^1$-$R^4$ = independently of one another, H, lower alkyl or lower hydroxyalkyl;
X = anion of an acid of $pK_A$ > 4 or the hydroxyl ion;
n = number of negative charges on the anion X The amines IIIa are generally known. The same is true of the ammonium salts IIIb (cf. Houben-Weyl, Methoden der Organischen Chemie (Methods of organic chemistry), 4th edition, Thieme Verlag, Stuttgart, volume 11/2, page 591 ff.).

As the anion X in the general formula IIIb, the carbonate ion and the hydrogencarbonate ion are preferred and the hydroxyl ion is particularly preferred.

As a rule, the amine IIIa or the ammonium salt IIIb is employed in an equimolar amount, based on bentazone (IIa). It can be advantageous for completing the reaction to use the amine IIIa or the ammonium salt IIIb in an excess. However, to achieve a complete conversion this excess in general does not need to exceed 10 mol %, based on IIa.

Suitable virtually water-immiscible organic solvents are: alkanes, preferably having 5 to 8 C atoms, especially n-alkanes such as n-pentane and n-hexane, and halohydrocarbons, preferably haloalkanes such as mono- and dichloroalkanes having 2 to 4 carbon atoms, such as 1,1-dichloroethane, 1,3-dichloropropane, 1,2-dichloropropane and in particular 1,2-dichloroethane.

In addition, mixtures of two or more of these virtually water-inmiscible organic solvents are also suitable.

A particularly preferred virtually water-immiscible organic solvent is 1,2-dichloroethane per se.

Based on one mol of bentazone (IIa), from 1 to 4 and especially from 1.5 to 3 kg of solvent are normally used.

The process can be carried out at from 20° to 80° C. The temperature during the reaction especially has an effect on the solubility of the bentazone (IIa), which increases with the temperature.

Especially in those cases where a gaseous or low-boiling amine IIIa is involved, however, the temperature should not exceed a value of 60° C. The reaction of bentazone IIa with If small amounts of the organic solvent are separated off with the aqueous phase here, these can be removed in a manner known per se before isolating the salt I, for example by stripping or, if appropriate, by azeotropic distillation, for example in the case of 1,2-dichloroethane/water as a reaction medium, at normal pressure or reduced pressure.

In order to take up the salt completely, as a rule, based on 1 kg of the salt I, from 1 to 5 kg, preferably from 2 to 4 kg, and in particular from 2.5 to 3.5 kg of water are used. The salt I usually precipitates at the reaction temperature. To complete the precipitation the solution is usually cooled. Crystallization is preferably carried out at from 5° to 40° C. and in particular at from 15° to 25° C.

A particular advantage of process B according to the invention is that in this manner the organic solvent, after it has been separated off from the aqueous phase, can be used immediately for further reactions without it having to be partially or totally evaporated to isolate the product and/or purified by distillation.

Using process B, on recycling the mother liquor the salt I can as a rule be obtained in a yield of from 98 to 100% with a purity of at least 98%.

Process B is particularly suitable for preparing the $NH_4^+$ salt of bentazone (I; $R^1$-$R^4$=H).

Process C

In process C bentazone (IIa) is reacted with an ammonium salt IIIb in water or the sodium salt of bentazone (IIb) is reacted with an ammonium salt IIIc in water (see scheme 3).

Scheme 3

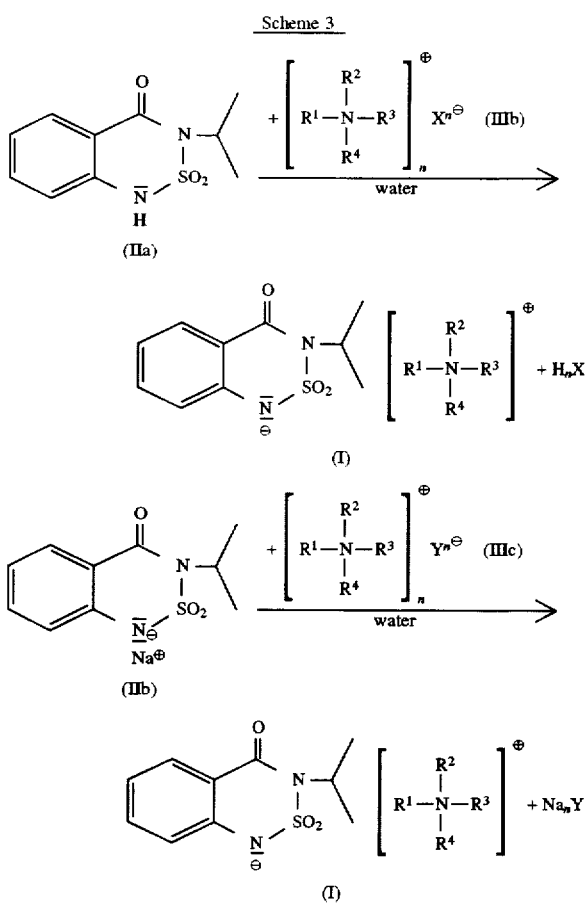

$R^1-R^4$ = independently of one another, H, lower alkyl or lower hydroxyalkyl;
Y = acid anion;
X = anion of an acid of $pK_A > 4$ or the hydroxyl ion;
n = number of negative charges on the anion X or Y Process C is particularly suitable for preparing the $NH_4^+$ salt of bentazone (I; $R^1-R^4$=hydrogen).

The ammonium salts IIIb are generally known (cf. Houben-Weyl, Methoden der Organischen Chemie (Methods of Organic Chemistry), 4th Edition, Thieme Verlag, Stuttgart, Volume 11/2, page 591 ff.).

Suitable anions Y in the general formula IIIc are: sulfate, hydrogensulfate, phosphate, hydrogenphosphate or dihydrogenphosphate, preferably halide or acetate and in particular chloride, nitrate, formate, carbonate and hydrogencarbonate.

The preferred acid anion Y in the general formula IIIc and the anion X of an acid of $pK_A>4$ are the carbonate ion and the hydrogencarbonate ion and the hydroxyl ion is particularly preferred for X.

As a rule, the ammonium salt IIIb, based on bentazone (IIa), and the ammonium salt IIIc, based on the sodium salt of bentazone (IIb), are employed in an equimolar amount. It can be advantageous for completing the reaction to use the ammonium salts in an excess. However, to achieve a complete conversion this excess in general does not need to exceed 10 mol %, based on IIa or IIb.

Based on one mol of bentazone (IIa) or its sodium salt IIb, from 0.2 to 4 kg and especially from 0.2 to 2 kg of water are normally used.

The sodium salt $Na_nY$ is usually more soluble in water than the salt I. If the latter therefore remains partially dissolved, it can be separated off by (fractional) crystallization. This procedure is familiar to the person skilled in the art, so further details on this point are unnecessary.

To achieve a good yield in the crystallization, a molar ratio of water to salt I of from 50:1 to 30:1 has proven particularly suitable.

The process can be carried out at from 10° to 80° C. The temperature during the reaction especially has an effect on the solubility of the bentazone (IIa) and its sodium salt IIb, which increases with the temperature. The reaction is preferably carried out at from 20° to 70° C., and in particular from 40° to 60° C.

The reaction is in general carried out at from 0.5 to 10 bar, preferably from 1 to 3 bar, and in particular at normal pressure (atmospheric pressure).

Suitable reactors are the apparatuses customarily suitable for reactions of this type.

Using process C, the salts I can as a rule be obtained in a yield of greater than 80% with a purity of at least 98%. By recycling the mother liquor, a yield of more than 98% can be achieved.

The salt I prepared by one of the processes A to C can be isolated in a manner known per se. In the case where it already crystallizes out of the reaction mixture, this especially occurs by filtration. If the salt is obtained in dissolved form, the entire solution can be freed from the solvent by a generally known process, for example by evaporation, especially at reduced pressure.

The salt I obtainable by processes B or C, which was crystallized from an aqueous phase, as a rule already contains less than 10% by weight of water.

As a rule, the damp (from organic solvent or water) salt I is dried at from 20° to 80° C., preferably 40° to 60° C. The drying can be carried out in customary drying apparatuses. It is preferably carried out under reduced pressure or with warming of the product I in a stream of air.

The mother liquors which remain after separation of crystallized salt I in some cases still contain up to 20% of the salt I in dissolved form. Where it is desired, the isolation of this dissolved active compound can be carried out in a manner known per se, for example by concentration of the solution and fresh crystallization or by complete evaporation of the mother liquor. Often, the mother liquor can also be fed back into the process again.

Granules of solutions of the salt I are obtained starting from the solutions resulting during preparation or the crystallization mother liquors are preferably obtained by a fluidized bed process or by agglomeration on a powder of I, which in turn was prepared by spray drying or vacuum drying.

The granules thus obtained customarily consist to from 20 to 100% by weight of salt I. The particle size of these granules is in general from 200 μm to 3000 μm. The dust content of the granules is low, being less than 20 mg for a 30 g sample (CIPAC MT 171: Dustiness of Granular Formulation), whereby high safety is achieved for the user. As a rule, the bulk weight of granules of this type is 400–800 g/l.

The salts I exhibit excellent storage behavior in water-soluble film bags. Film bags of this type are known per se (EP-A 449 773, EP-A 493 553), so further details on this point are unnecessary.

The filled film bags customarily contain from 0.1 to 10 kg, preferably from 0.5 to 5 kg, of active compound I. The thickness of the films is from 20 to 100 μm, preferably from 30 to 60 μm. The water content in the polymer films can be up to 20% by weight.

Apart from the salts I, the granules obtained as described above or the filled film bags can contain yet other customary additives, eg. surface-active substances, fillers or even other crop protection active compounds.

It has been found that the salts I, and especially the $NH_4^+$ salt of bentazone, have a relatively low solubility in the respective reaction media, compared with the starting substances IIa or IIb. This effect is used in the processes according to the invention in order to isolate the product I from the reaction mixture in solid form in a simple manner.

However, the ammonium salts and particular ly the $NH_4^+$ salt dissolve distinctly more rapidly in water compared with the sodium salt usually used, and thus the cost of the preparation of aqueous active compound mixtures is decreased.

EXAMPLES

Example 1

1.7–3 g of ammonia were introduced as a gas with stirring at 20°–50° C. into a solution of 24 g of bentazone (IIa) in 2376 g of 1,2dichloroethane, a suspension being formed. The solid was separated off at 20° C. by filtration and freed from solvent residues under reduced pressure. 25.4 g of bentazone-ammonium (m.p. 180° C.) were obtained.

Example 2.

1.7 g of ammonia were introduced as a gas at 30°–50° C. with stirring into a solution of 24 g of bentazone (IIa) in 16 g of acetone. Bentazone-ammonium was deposited and was filtered off at room temperature. The crystallisate obtained was freed from the solvent under reduced pressure and at 50° C. 19.5 g of bentazone-ammonium were obtained. The mother liquor from the filtration was evaporated to dryness under reduced pressure and at 50° C., and a further 6 g of bentazone-ammonium remained.

Example 3

4.8 g of ammonium carbonate were introduced with stirring into a suspension of 24 g of bentazone (IIa) and 300 g of water. The reaction mixture was subsequently stirred at 50° C. for 2 hours and freed from solid particles by filtration. After evaporating the solution under reduced pressure, 25.5 g of bentazone-ammonium remained.

Example 4

The procedure was as in Example 3, but 7.9 g of ammonium hydrogen carbonate were used instead of ammonium carbonate. 25.5 g of bentazone-ammonium were obtained.

Example 5

8 g of ammonium nitrate were introduced at 50° C. with stirring into a solution of 26.3 g of bentazone-sodium in 21.7 g of water, and the reaction mixture was subsequently stirred for a further hour. After cooling to 20° C., the precipitate was filtered off, washed twice with 5 ml of ice water in each case and dried under reduced pressure and at 50° C. 18.9 g of bentazone-ammonium of 99% purity were obtained.

Example 6

The reaction was carried out as described in Example 5, but 6.3 g of ammonium formate were employed instead of the ammonium nitrate. The yield of bentazone-ammonium was 21 g. The product had a purity of 98.4%.

Example 7

A solution of 24 g of bentazone (IIa) in 216 g of 1,2-dichloroethane was treated with stirring at 50°–60° C. with 34 g of ammonia water (5% strength solution of ammonia in water). After addition was complete, the aqueous phase was separated off at 50°–60° C. On cooling the aqueous phase, the bentazone-ammonium was deposited in crystalline form. The solid was separated off at 20° C. by filtration and freed from solvent residues under reduced pressure and at 50° C. 11.8 g of bentazone-ammonium (m.p. 180° C.) were obtained. By evaporating the water from the mother liquor under reduced pressure and at 50°–60° C., a further 13.7 g of bentazone-ammonium were obtained.

Example 8

A solution of 24 g of bentazone (IIa) in 216 g of 1,2-dichloroethane was treated with 22.5 g of a 20% strength aqueous solution of dimethylamine with stirring at 30°–50° C. After addition was complete, the aqueous phase was separated off at 50°–60° C. and evaporated to dryness under reduced pressure and at 50°–60° C. 28 g of bentazone-dimethylammonium (m.p. 145°–147° C.; purity >99% according to HPLC analysis for bentazone and titration for dimethylammonium) were obtained.

Example 9

A mixture of 24 g of bentazone (IIa), 4.8 g of ammonium carbonate, 220 g of 1,2-dichloroethane and 300 g of water was stirred at 50°–60° C. for 1 hour. The phases were then separated, and the water was removed under reduced pressure and at 50°–60° C. 25.5 g of bentazone-ammonium were obtained.

Example 10

Corresponding to Example 9, but using 7.9 g of ammonium hydrogen-carbonate, 25.5 g of bentazone-ammonium were obtained.

Example 11

A 20% strength aqueous solution of bentazone-ammonium was dried in a fluidized bed spray granulator at a drying air temperature of 120° C. In this process, the ammonium salt solution was introduced as a jet and granular particles were formed by agglomeration and drying. The granules obtained contained 99.6% by weight of bentazone-ammonium and had a residual water content of 0.4% by weight. The mean particle size of the granules was 0.3 mm (maximum diameter). The granules obtained were dust-free and dissolved rapidly in water. They were additionally nonhygroscopic, ie. they remained flowable even on relatively long storage in damp air.

Example 12

A fluidized bed spray granulator was charged with 75 g of ammonium sulfate powder. 375 g of a 20% strength by weight aqueous solution of bentazone-ammonium were then introduced as a jet into the granulator previously prepared in this way at a drying air temperature of 120° C. Granular particles were formed by agglomeration and drying. The granules obtained contained 50% by eight of bentazone-ammonium and had a residual water content of 0.1–0.5% by weight. The mean particle size of the granules was 1–2 mm (maximum diameter). The granules obtained were dust-free and dissolved rapidly in water. They were additionally nonhygroscopic, ie. they remained flowable even on relatively long storage in moist air.

Example 13

Physical behavior of the products a) Investigation of the hygroscopicity of the salts 1 g of the sample in each case was dried in vacuo at 50° C. for 48 hours. The dried samples were stored at 55% and 65% relative atmospheric humidity and 20° C. and the weight increase of the samples was measured after the equilibrium state had been reached. The flow properties of the samples and their appearance were also assessed. With respect to the hygroscopicity, critical substances absorbed a lot of water from the air until the equilibrium state was reached. This led to caking of the substances. The results are compiled in the following table.

| Type of salt | Relative atmospheric humidity [%] | Weight increase [%] | Properties after storage |
|---|---|---|---|
| Sodium salt | 55 | 12.6% | formed lumps, caked |
| Potassium salt | 55 | 6.7% | formed lumps, caked |
| Potassium salt | 55 | 12.0% | formed lumps, caked |
| Ammonium salt | 55 | 0.5% | crystalline, flowable |
|  | 65 | 0.5% | crystalline, flowable | b) Investigation of the behavior of the salts in the film bag:

10 g of substance in the form of granules were in each case eat-sealed into film bags. The filled film bags (film: Monosol 8030, manufacturer: Chris Craft Inc., USA) were then stored at various temperatures in water vapor-resistant outer protective packaging for 4 weeks. The stability of the films was expressed by the elasticity of the films on mechanical stress. If water was absorbed from the film by the bentazone salt, the film became brittle. For example, the Monosol 8030 film lost a large part of the residual moisture contained in the film in the presence of bentazone-sodium in a closed container. At room temperature this decreased from initially 14% to 6% in the equlibrium state. The result was embrittlement of the film and failing of the bag on mechanical stress such as transport, impact and loading. The results of model experiments are compiled in the following table.

| Type of salt | T | Properties of the film bag |
|---|---|---|
| Sodium salt | 20 | brittle, friable |
|  | 30 | brittle, friable |
| Ammonium salt | 20 | elastic, stable |
|  | 30 | elastic, stable |

We claim:

1. A process for preparing salts of 3-isopropyl-2,1,3-benzothiadiazin-4-one 2,2-dioxide of the general formula I

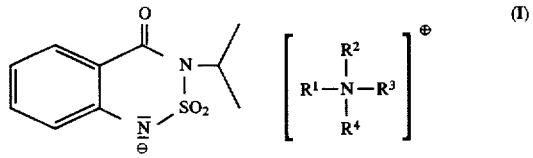

where the radicals $R^1$, $R^2$ and $R^3$ independently of one another are hydrogen, lower alkyl or lower hydroxyalkyl, which comprises reacting 3-isopropyl-2,1,3-benzothiadiazin-4-one 2,2-dioxide (IIa)

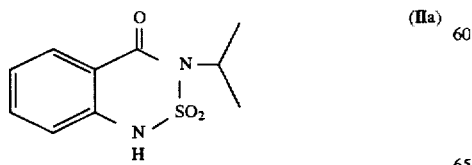

in an organic solvent with an amine of the general formula IIIa

2. A process as claimed in claim 1, wherein an amine IIIa is used where the radicals $R^1$, $R^2$ and $R^3$ are hydrogen.

3. A process as claimed in claim 1 wherein the organic solvent used is 1,2-dichloroethane.

4. A process for preparing salts of 3-isopropyl-2,1,3-benzothiadiazin-4-one 2,2-dioxide of the general formula I

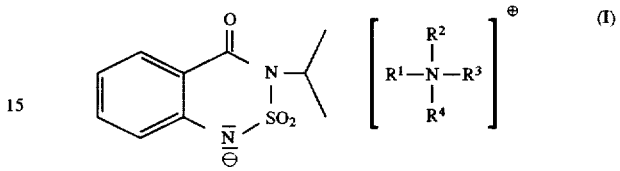

where the radicals $R^1$, $R^2$, $R^3$ and $R^4$ independently of one another are hydrogen, lower alkyl or lower hydroxyalkyl, which comprises a) reacting 3-isopropyl-2,1,3-benzothiadiazin-4-one 2,2-dioxide (IIa)

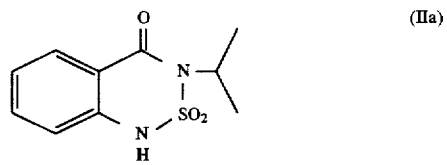

in a virtually water-immiscible organic solvent and, if desired, in the presence of water, with an amine of the general formula IIIa

or an ammonium salt of the general formula IIIb

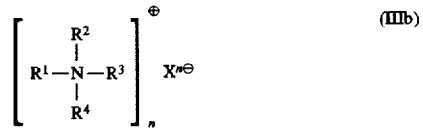

where X is the anion of an acid of $pK_A$ greater than 4 or the hydroxyl ion and n is equal to the number of negative charges on the anion X, and b) taking up the salt I in water.

5. A process as claimed in claim 4, wherein the organic solvent used is 1,2-dichloroethane.

6. A process as claimed in claim 4 wherein an amine IIIa or ammonium salt IIIb is employed where the radicals $R^1$ to $R^4$ are hydrogen.

7. A process for preparing salts of 3-isopropyl-2,1,3-benzothiadiazin-4-one 2,2-dioxide of the general formula I

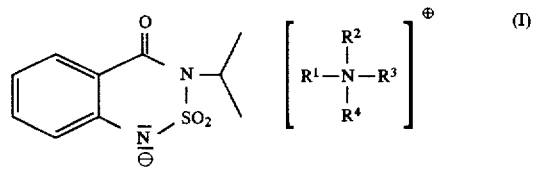

where the radicals $R^1$, $R^2$, $R^3$ and $R^4$ independently of one another are hydrogen, lower alkyl or lower hydroxyalkyl, which comprises a) reacting 3-isopropyl-2,1,3-benzothiadiazin-4-one 2,2-dioxide (IIa)

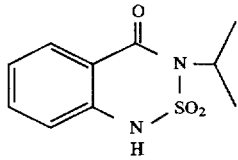
(IIa)

in water with an ammonium salt of the general formula IIIb

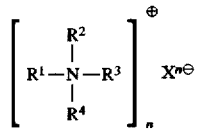
(IIIb)

where X is the anion of an acid having a $PK_A$ greater than 4 or the hydroxyl ion and n is equal to the number of negative charges on the anion X, or b) reacting the sodium salt of 3-isopropyl-2,1,3-benzothiadiazin-4-one 2,2-dioxide (IIb)

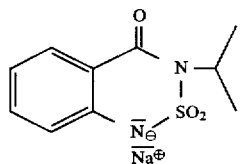
(IIb)

in water with an ammonium salt of the general formula IIIc

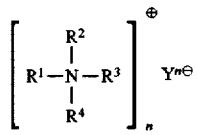
(IIIc)

where Y is the anion of an acid and n is equal to the number of negative charges on the anion Y.

8. A process as claimed in claim 7, wherein the ammonium salt IIIb contains the hydroxyl ion as the anion X.

9. A process as claimed in claim 7, wherein the ammonium salt IIIc contains the carbonate or the hydrogencarbonate ion as the anion Y.

* * * * *